United States Patent
Druzhinin

(10) Patent No.: US 9,750,780 B2
(45) Date of Patent: Sep. 5, 2017

(54) AQUEOUS-LIPIDIC CAROTENOID-CONTAINING COMPOSITIONS

(76) Inventor: Dmitry Druzhinin, Moscow (RU)

(*) Notice: Subject to any disclaimer, the term of this patent is extended or adjusted under 35 U.S.C. 154(b) by 159 days.

(21) Appl. No.: 14/411,279

(22) PCT Filed: Jun. 25, 2012

(86) PCT No.: PCT/RU2012/000500
§ 371 (c)(1),
(2), (4) Date: Dec. 24, 2014

(87) PCT Pub. No.: WO2014/003594
PCT Pub. Date: Jan. 3, 2014

(65) Prior Publication Data
US 2015/0140144 A1    May 21, 2015

(51) Int. Cl.
| | | |
|---|---|---|
| *A61K 36/00* | (2006.01) | |
| *A61K 36/81* | (2006.01) | |
| *A23K 20/174* | (2016.01) | |
| *A23K 20/179* | (2016.01) | |
| *A23K 20/163* | (2016.01) | |
| *A23L 33/105* | (2016.01) | |
| *A23L 33/155* | (2016.01) | |
| *A23L 33/21* | (2016.01) | |

(52) U.S. Cl.
CPC ............ *A61K 36/81* (2013.01); *A23K 20/163* (2016.05); *A23K 20/174* (2016.05); *A23K 20/179* (2016.05); *A23L 33/105* (2016.08); *A23L 33/155* (2016.08); *A23L 33/21* (2016.08); *A23V 2002/00* (2013.01)

(58) Field of Classification Search
None
See application file for complete search history.

(56) References Cited

U.S. PATENT DOCUMENTS

2008/0255247 A1* 10/2008 Sagalowicz et al. ......... 514/772
2010/0233342 A1*  9/2010 Almeida Rivera ..... A23L 1/308
                                                    426/589

FOREIGN PATENT DOCUMENTS

ES    WO 03051138 A1 *  6/2003 ............. A23L 19/01

OTHER PUBLICATIONS

Navarro-Gonzalez et al, Chemical profile, functional and antioxidant properties of tomato peel fiber. Food research international (2011), vol. 44, No. 5, pp. 1528-1535.*

* cited by examiner

*Primary Examiner* — Qiuwen Mi

(57) ABSTRACT

The invention provides a primary carotenoid-containing composition comprising an aqua-containing component, a lipid-containing component and a carotenoid-containing fiber material from plant origin with lowered content of aqua-soluble substances. The invention also provides oral compositions that comprise the primary composition in a foodstuff, in a food supplement or in a pharmaceutical preparation.

20 Claims, No Drawings

AQUEOUS-LIPIDIC CAROTENOID-CONTAINING COMPOSITIONS

FIELD OF THE INVENTION

The invention relates to the field of carotenoid-containing compositions. These compositions can be used in or as a foodstuff, a food supplement or a pharmaceutical preparation.

BACKGROUND OF THE INVENTION

Most of the carotenoid-containing functional food, food supplement and pharmaceutical products available in the market contain carotenoids obtained using organic solvents by extraction from plant materials, biotechnologically or by organic synthesis process and do not contain dietary fiber from carotenoid-containing plant material, although the latter has important health, gustatory and technological benefits discussed below. Another problem with these carotenoid-containing products is that they require organic solvents for their manufacturing. However, total elimination of organic solvents from the resulting product cannot be guaranteed. At the same time, presence of organic solvents traces in the product is definitely undesirable for the consumers. Also, organic solvents are hazardous for those involved in the manufacturing process and for the environment (U.S. Pat. No. 7,557,146 B2, U.S. 2004/0131733 A1).

It has been proposed to produce carotenoid-containing products free of organic solvents using supercritical carbon dioxide for extraction from carotenoid-containing plant material (U.S. 2004/0131733 A1, U.S. 2009/0304870 A1). However, dietary fiber from carotenoid-containing plant material is not included in the resulting carotenoid-containing products. Also, the manufacturing process is expensive, includes the agent foreign to the resulting product and may be negative for the environment through the greenhouse effect.

Dietary fiber from carotenoid-containing plant material is not included in the carotenoid-enriched oil, proposed in the U.S. Pat. No. 7,557,146 B2, forming waste solid residue.

There is a need for carotenoid-containing composition which would contain dietary fiber from carotenoid-containing plant material as an important health resource as well as gustatory and technologically important thickening component. And it would be highly desirable that this composition would have increased bioefficiency providing enhanced health benefits.

OBJECT OF THE INVENTION

An object of the invention is a carotenoid-containing composition containing dietary fiber from carotenoid-containing plant material which would have increased bioefficiency. Another object of the invention is oral compositions comprising said primary composition.

DETAILED DESCRIPTION OF THE INVENTION

The primary invention composition, further referred to as "invention composition", is a composition comprising an aqua-containing component, a lipid-containing component and a carotenoid-containing fiber material from plant origin with lowered content of aqua-soluble substances. An aqua-containing component may also be a lipid-containing component of the invention composition and vice verse, such as, for example, many aqua-containing lipid-containing dairy products. A carotenoid-containing fiber material may contain aqua and/or lipid and as such also may be an aqua-containing and/or a lipid-containing component of the invention composition. The rare example of the lipid-containing carotenoid-rich fruit is gac fruit containing fatty acids (Ishida B K et al. (2004). Fatty acid and carotenoid composition of gac (*Momordica cochinchinensis* Spreng) fruit. J. Agric. Food. Chem. 52 (2): 274-9). An aqua-containing component may be aqua. A lipid-containing component may be a lipid.

One component of the invention composition is a carotenoid-containing fiber material from plant origin. Important positive role of dietary fiber for human health is well-known from the prior art and its intake is known as providing many health benefits. Individuals with high intakes of dietary fiber appear to be at significantly lower risk for developing coronary heart disease, stroke, hypertension, diabetes, obesity, and certain gastrointestinal diseases. Increasing fiber intake lowers blood pressure and serum cholesterol levels. Increased intake of soluble fiber improves glycemia and insulin sensitivity in non-diabetic and diabetic individuals. Fiber supplementation in obese individuals significantly enhances weight loss. Increased fiber intake benefits a number of gastrointestinal disorders including the following: gastroesophageal reflux disease, duodenal ulcer, diverticulitis, constipation, and hemorrhoids. Prebiotic fibers appear to enhance immune function. Dietary fiber intake provides similar benefits for children as for adults. The recommended dietary fiber intakes for children and adults are 14 g/1000 kcal. However, average fiber intakes for US children and adults are less than half of the recommended levels. More effective communication and consumer education is required to enhance fiber consumption from foods or supplements (Anderson J W, et al. (2009 April). Health benefits of dietary fiber. Nutr. Rev. 67(4):188-205).

Also dietary fiber is a natural thickening agent significant for the invention composition texture, bulk and viscosity. It is common practice in the food industry to use additives such as starch, pectin, guar gum, xanthan gum and others to control texture, bulk and viscosity and prevent syneresis in the food products containing plant materials. However, using of additives which are foreign to the biologically active carotenoid-containing component, may have their own biological activity profile absolutely different from the biological activity profile of carotenoids, may be an additional source of product contamination with pollutants such as agrochemicals, is definitely undesirable for the consumers interested to receive 100% natural product. In the invention composition texture, bulk and viscosity of the composition are easily controllable through aqua, lipid and plant material dietary fiber content ratios.

Carotenoid-containing fiber material from plant origin may be from tomatoes, carrots, peaches, apricots, oranges, melons, guavas, papayas, grapefruits, pineapples, grapes, gac fruits, kiwifruits or from other plants. It may be from one plant or may be a combination of carotenoid-containing fiber materials from two or more different plants. It may be from fruits, vegetables, berries, roots and other parts of the plant. It may be in a form of a pulp, a concentrate, a puree or a dried material, in a form of a powder or in another form, for example, in a form of a solid part resulting from plant origin concentrate centrifugation or filtration.

The invention composition lipid may be animal fat, animal oil, fish fat, fish oil, milkfat, vegetable fat, vegetable oil or another lipid or a combination of any of thereof. The vegetable ail may be corn oil, olive oil, sunflower oil, soya oil, rapeseed oil, palm oil or another one. Invention composition lipid-containing component may be, for example, a dairy product, vegetable oil, fish oil or a combination of any of thereof.

Aqua, dietary fiber, lipid and carotenoids work synergistically as components of the invention composition. Aqua absorbed in the dietary fiber ensures necessary texture, bulk and viscosity of the invention composition as well as dietary fiber proper absorption and health function in the gastrointestinal tract. Aqua content in the invention composition may vary; preferably, it may be within the range from 10% to 90% and, most preferably, within the range from 20% to 85%.

Lipid is mostly responsible for carotenoids bioavailability as liposoluble substances. Specifically, aqua-lipid combination may play important favorable role for lipid droplets formation in which liposoluble carotenoid may migrate into intestinal mucosal cells during intestine absorption (Boileau T. W.-M. et al. (2002). Bioavailability of all-trans and cis-isomers of lycopene. Experiment. Biol. Med. 227: 914-919) through formation of direct emulsions from diluted to highly concentrated in the invention composition or, also, during invention composition intestine absorption process. For example, carotenoid can remain dissolved in supersaturated concentration in the oil droplets of oil/aqua emulsions if the droplet size is small enough (Bunnell R. H. (1958). Coloring water-base foods with β-carotene. Food. Technol. 12:536-541; EP 0800824 A1). Lipid/aqua content ratio in the invention composition may vary; preferably, it is in the range from 1:1000 to 99:1 and, most preferably, in the range from 1:10 to 5:1. Finally, carotenoids determine the invention composition bioefficiency profile.

Lowering of the aqua-soluble substances content in the invention composition carotenoid-containing fiber material from plant origin, such as, for example, tomato or pineapple concentrate, drastically changes the taste of the invention composition and comprising said primary composition oral compositions. Aqua-soluble substances are mostly responsible for the natural taste which is characteristic to the specific carotenoid-containing fiber material from plant origin. Lowering of the aqua-soluble substances content in said fiber material imparts neutral taste to containing it invention composition which has nothing resembling the taste of the original fiber material. Additional ingredients may be added to the invention composition in order to impart a desired taste, biological activity or other characteristics of said composition. An additional ingredient may be an egg component or product, for example, to obtain a mayonnaise type product. An emulsifying agent can be added to the invention composition as an additional ingredient to stabilize it in the form of emulsion. A dairy product, wheat or wheat component or product may be additional ingredients as well.

Proposed lowering of the aqua-soluble substances content of the invention composition carotenoid-containing fiber material from plant origin is contrary to the common use of plant materials in foodstuffs not only because of gustatory characteristics change discussed above but also because plant materials are generally considered to be a good source of aqua-soluble vitamins, minerals and other aqua-soluble biologically active substances.

Lowering of the aqua-soluble substances, content in the carotenoid-containing fiber material from plant origin can be performed using fiber material homogenization with aqua or aqua-containing component and subsequent phase separation using centrifugation, decantation, filtration or by other means. The process may be repeated to achieve the required degree of aqua-soluble substances content lowering. Further process of the invention composition manufacturing may include homogenization of said fiber material with other components of the invention composition. Organic solvents are not required for the manufacturing of the invention composition.

The invention composition may be a component of an oral composition. Said oral composition constitutes a part of the invention and may be in a form of a foodstuff, a food supplement, a pharmaceutical preparation or in another form. The content of the invention composition in said oral composition may vary; preferably, the content may be from 1% to 100% and, most preferably, from 10% to 90%. A foodstuff may be in a form of a dairy product, a sauce, mayonnaise, a salad dressing, a yogurt, an infant nutritional product, a dietary supplement, a puree, a liquid drink, a pet food product or another type of a foodstuff.

If an oral composition comprises the lycopene-containing invention composition the lycopene content in said oral composition may vary; preferably, it may be from 5 mg to 150 mg per 100 g of an oral composition.

The unexpected result of the invention is that the invention composition which according to the invention includes carotenoid-containing fiber material from plant origin with lowered content of aqua-soluble substances has increased bioefficiency comparing to the composition in which the content of the aqua-soluble substances in the carotenoid-containing fiber material from plant origin is not lowered. This unexpected result is described in the preferred embodiment of the invention in Example 1 in relation to the invention composition bioefficiency towards semen characteristics improvement resulting from tomato carotenoid-containing invention composition intake by men with idiopatic infertility. The tomato fiber material contains carotenoids lycopene, phytoene, phytofluene, alpha-carotene, beta-carotene, gamma-carotene, zeta-carotene, lutein, astaxanthin, canthaxanthin, zeaxanthin and other carotenoids.

The fundamental mechanism of carotenoids bioefficiency is generally the same for all carotenoids which is not surprising as they have close chemical structure and role in plant biological processes. Chemically they are liposoluble tetraterpenoids containing 40 carbon atoms grouped in four monoterpene units 10 carbon atoms in each. Biologically all carotenoids are organic pigments originating in the chromoplasts and chloroplasts within plant cells supported by the plant fiber and participating in light absorption, energy transfer and antioxidation protection.

The fundamental mechanism of all carotenoids bioefficiency is ROS quenching, i.e., their capability to efficiently quench reactive oxygen species (ROS) which contain highly reactive oxygen radicals and are involved in cell membranes lipid peroxidation (A. T. Diplockl, et. al. (1998). Functional food science and defense against reactive oxidative species. British Journal of Nutrition; 80, Suppl. 1, S77-S112). ROS are supposed to be the important factor of different pathological processes including atherosclerosis, male infertility, etc. ROS is hypothesized to cause its effects on sperm function through peroxidation of polyunsaturated fatty acids in the spermatozoa membranes (Gupta N. P., Kumar R. (2002). Lycopene therapy in idiopatic male infertility—a preliminary report. Int. Urol. and Nephrol. 34: 369-372). Spermatozoa membranes are especially vulnerable to lipid-related damage.

ROS quenching is supposed to be the mechanism behind carotenoid lycopene bioefficiency towards semen characteristics improvement through significant protection of sperm from peroxidative damage (Ibid.) as well as behind Example 1 tomato carotenoid-containing invention composition bioefficiency towards semen characteristics improvement said bioefficiency being increased when the content of aqua-soluble substances in the carotenoid-containing fiber material of the invention composition is lowered. The most abundant tomato carotenoid lycopene displays the highest ROS quenching ability among carotenoids (Di Mascio P., et. al. (1989). Lycopene as the most efficient biological carotenoid singlet oxygen quencher. Arch. Biochem. Biophys. 274 (2): 532-8).

On the other side, carotenoid-containing fiber materials from plant origin, for example, from tomatoes, oranges, grapefruits, peaches, papayas, pineapples and others, generally contain the same variety of aqua-soluble substances such as aqua-soluble mineral substances, salts, organic acids, sugars, amino acids. That gives basis to consider the effect of the increased bioefficiency of the invention composition comprising carotenoid-containing fiber material from plant origin with lowered content of aqua-soluble substances to be inherent in said carotenoid-containing composition in general.

The preferred (best mode) embodiment of the invention is illustrated by the Example 1.

Example 1

Preparation of the Invention Composition and its Use

Tomato concentrate is homogenized with aqua and centrifuged at 6000 rpm for 20 min. The solid part after centrifugation is homogenized with aqua and centrifuged again.

After centrifugation the resulting solid part is carotenoid lycopene-containing tomato fiber material which has 10 times lowered content of aqua-soluble substances comparing to fiber material obtained by centrifugation of tomato concentrate under the same condition, i.e., at 6000 rpm for 20 min, but without foregoing homogenization with aqua and used for the comparative product preparation described below. Tomato fiber material has 80% aqua content and 810 ppm HPLC (High Performance Liquid Chromatography) lycopene content. To prepare the invention composition tomato fiber material with 10 times lowered content of aqua-soluble substances is homogenized with virgin corn oil added to the fiber material in the proportion 50:73. The product obtained is further referred to as L-product (product with lowered content of aqua-soluble substances). It contains 47.4% of aqua, 40.6% of lipid; the lipid/aqua content ratio is approximately 86:100. The rest 12% of L-product include tomato fiber, other tomato aqua-insoluble solids and lowered content tomato aqua-soluble solids. L-product contains 48 mg of lycopene per 100 g of the product. The product is stored in a refrigerator.

For the comparative product preparation tomato concentrate is centrifuged at 6000 rpm for 20 min. After centrifugation the resulting solid part is lycopene-containing tomato fiber material in which the content of aqua-soluble substances is not lowered. Tomato fiber material has 80% aqua content and 810 ppm HPLC lycopene content. To obtain the comparative product said tomato fiber material is homogenized with virgin corn oil added to the fiber material in the proportion 50:73. The product obtained is further referred to as R-product (product in which the content of aqua-soluble substances is not lowered). R-product contains 48 mg of lycopene per 100 g of the product. The product is stored in a refrigerator.

A test of L-product bioefficiency comparing to R-product bioefficiency has been performed in men with idiopatic infertility. As discussed above, the improvement of semen parameters using carotenoid therapy has been demonstrated in the prior art.

28 men with diagnosed idiopatic infertility, age 30-42, who volunteered to consume the foodstuff for improving the semen parameters, were divided into two groups, L-group and R-group, 14 men in each group. Sperm concentration and progressive motility were tested according to WHO laboratory manual for the examination and processing of human semen, 5th edition.

In the L-group 25 grams of L-product containing 12 mg of lycopene were consumed daily by those included in the group for a period of 60 days. Sperm concentration and progressive motility were tested at baseline and after 60 days of L-product intake.

In the R-group 25 grams of R-product containing 12 mg of lycopene were consumed daily by those included in the group for a period of 60 days. Sperm concentration and progressive motility were also tested at baseline and after 60 days of R-product intake.

According to the results of the baseline test in L-group baseline mean sperm concentration was 13.9 million/ml, mean progressive motility was 17.2%. After 60 days of L-product intake mean sperm concentration was 42 million/ml, mean progressive motility 60.5%. The mean sperm concentration improvement was 28.1 million/ml, the mean progressive motility improvement was 43.3%.

According to the results of the baseline test in R-group mean baseline sperm concentration was 12.8 million/ml, mean progressive motility 15.3%. After 60 days of R-product intake mean sperm concentration was 33.7 million/ml, mean progressive motility 45.3%. The mean sperm concentration improvement was 20.9 million/ml, the mean progressive motility improvement was 30%.

As one can see from the results of the comparative study the mean sperm concentration improvement in L-group was 7.2 million/ml higher than in R-group. The mean progressive motility improvement difference between groups was 13.3%, also with better result in L-group.

The results of the comparative study show that L-product which includes carotenoid-containing fiber material from plant origin with lowered content of aqua-soluble substances has statistically significant ($p<0.05$) increased bioefficiency comparing to R-product which includes carotenoid-containing fiber material from plant origin wherein the content of aqua-soluble substances is not lowered. An effect of increased bioefficiency of the invention composition having lowered content of aqua-soluble substances in the carotenoid-containing fiber material from plant origin of said composition therefore clearly exists.

No doubt that the primary invention composition and comprising it oral compositions can be used for health benefit not only by men with idiopathic infertility but in all areas where carotenoids, dietary fiber and other biologically active components of said compositions are desirable including cardiovascular diseases prevention and treatment, benign prostate hyperplasia, prevention and treatment of cancer, UV-protection of skin and skin care, cell aging, hair growth and other areas as, probably, the very healthy bio-efficient alternative choice to products containing carotenoids obtained using organic solvents by extraction from plant materials, biotechnologically or by organic synthesis process, supercritical carbon dioxide carotenoid-containing products and other carotenoid-containing functional food, food supplement and pharmaceutical products available in the market.

It should be noted that the above-mentioned embodiment and example illustrate rather than limit the invention, and that those skilled in the art will be able to design many alternative embodiments without departing from the scope of the appended claims. Use of the verb "to comprise" and its conjugations does not exclude the presence of elements or steps other than those stated in a claim. The article "a" or "an" preceding an element does not exclude the presence of a plurality of such elements. The mere fact, that certain elements are recited in mutually different dependent claims does not indicate that a combination of these elements cannot be used to advantage. The dimensions and values disclosed herein are not to be understood as being strictly limited to the exact numerical values recited. Instead, unless otherwise specified, each such dimension is intended to mean both the recited value and a functionally equivalent range surrounding that value. For example, a value disclosed as "10%" is intended to mean "about 10%".

The invention claimed is:

1. Carotenoid lycopene-containing food composition from tomato concentrate characterized in that said composition is lacking tomato taste, said composition comprising an aqua-containing component, lipid, and tomato concentrate which is processed to provide 10 or more times lowered content of aqua-soluble substances in said tomato concentrate as compared to said content in said tomato concentrate without said processing wherein:
   (a) aqua content in said tomato concentrate is not increased as a result of said processing;
   (b) as a result of said processing processed tomato concentrate has no tomato taste;
   (c) aqua content in said composition is from 20% to 90% of said composition by weight and lipid/aqua content ratio in said composition is from 1:1000 to 5:1.

2. A composition according to claim 1 wherein as a result of said processing the content of an aqua-soluble substance in tomato concentrate is lowered 10 or more times as compared to said content in said tomato concentrate without said processing and wherein an aqua-soluble substance is selected from the group consisting of an aqua-soluble mineral substance, an aqua-soluble salt, an aqua-soluble acid, an aqua-soluble sugar or a combination of any of thereof.

3. A composition according to claim 1 wherein tomato concentrate is also an aqua-containing component of said composition.

4. A composition according to claim 3 wherein lipid is vegetable oil.

5. A composition according to claim 4 wherein as a result of said processing the content of an aqua-soluble substance in tomato concentrate is lowered 10 or more times as compared to said content in said tomato concentrate without said processing and wherein an aqua-soluble substance is selected from the group consisting of an aqua-soluble mineral substance, an aqua-soluble salt, an aqua-soluble acid, an aqua-soluble sugar or a combination of any of thereof.

6. A composition according to claim 1 wherein one or more additional ingredients are added to said composition.

7. A composition according to claim 1 wherein an aqua-containing component is aqua and lipid is vegetable oil.

8. A composition according to claim 7 wherein as a result of said processing the content of an aqua-soluble substance in tomato concentrate is lowered 10 or more times as compared to said content in said tomato concentrate without said processing and wherein an aqua-soluble substance is selected from the group consisting of an aqua-soluble mineral substance, an aqua-soluble salt, an aqua-soluble acid, an aqua-soluble sugar or a combination of any of thereof.

9. A composition according to claim 1 wherein carotenoid lycopene content in said composition is from 5 mg to 150 mg per 100 g of said composition.

10. A composition according to claim 9 wherein lipid/aqua content ratio in said composition is from 1:10 to 5:1.

11. A composition according to claim 1 wherein lipid/aqua content ratio in said composition is from 1:10 to 5:1.

12. An oral composition which comprises carotenoid lycopene-containing food composition from tomato concentrate characterized in that said food composition is lacking tomato taste, said food composition comprising lipid and tomato concentrate which is processed to provide 10 or more times lowered content of aqua-soluble substances in said tomato concentrate as compared to said content in said tomato concentrate without said processing wherein:
   (a) the content of aqua in said tomato concentrate is not increased as a result of said processing;
   (b) as a result of said processing processed tomato concentrate has no tomato taste;
   (c) the content of said food composition in said oral composition is from 1% to 100% of said oral composition.

13. An oral composition according to claim 12 wherein the content of said food composition in said oral composition is from 10% to 90% of said oral composition.

14. An oral composition according to claim 13 wherein carotenoid lycopene content in said oral composition is from 5 mg to 150 mg per 100 g of said oral composition.

15. An oral composition according to claim 12 wherein carotenoid lycopene content in said oral composition is from 5 mg to 150 mg per 100 g of said oral composition.

16. Carotenoid lycopene-containing food composition from tomato concentrate characterized in that said composition is lacking tomato taste, said composition comprising vegetable oil and tomato concentrate which is processed to provide 10 or more times lowered content of aqua-soluble substances in said tomato concentrate as compared to said content in said tomato concentrate without said processing wherein:
   (a) aqua content in said tomato concentrate is not increased as a result of said processing;
   (b) as a result of said processing processed tomato concentrate has no tomato taste;
   (c) aqua content in said composition is from 20% to 90% of said composition by weight and lipid/aqua content ratio in said composition is from 1:1000 to 5:1.

17. A composition according to claim 16 wherein one or more additional ingredients are added to said composition.

18. A composition according to claim 16 wherein carotenoid lycopene content in said composition is from 5 mg to 150 mg per 100 g of said composition.

19. A composition according to claim 16 wherein as a result of said processing the content of an aqua-soluble substance in tomato concentrate is lowered 10 or more times as compared to said content in said tomato concentrate without said processing and wherein an aqua-soluble substance is selected from the group consisting of an aqua-soluble mineral substance, an aqua-soluble salt, an aqua-soluble acid, an aqua-soluble sugar or a combination of any of thereof.

20. A composition according to claim 16 wherein lipid/aqua content ratio in said composition is from 1:10 to 5:1.

* * * * *